United States Patent
Ninomiya et al.

(10) Patent No.: US 7,505,126 B2
(45) Date of Patent: Mar. 17, 2009

(54) METHOD AND DEVICE FOR MONITORING HYDROGEN GAS AND HYDROGEN FLAME

(75) Inventors: Hideki Ninomiya, Takamatsu (JP); Koji Ichikawa, Takamatsu (JP); Hirofumi Miki, Takamatsu (JP); Tasuku Moriya, Takamatsu (JP)

(73) Assignee: Shikoku Research Institute Incorporated, Takamatsu-shi (JP)

( * ) Notice: Subject to any disclaimer, the term of this patent is extended or adjusted under 35 U.S.C. 154(b) by 536 days.

(21) Appl. No.: 10/567,346

(22) PCT Filed: Jun. 9, 2004

(86) PCT No.: PCT/JP2004/008038

§ 371 (c)(1),
(2), (4) Date: Feb. 6, 2006

(87) PCT Pub. No.: WO2005/015183

PCT Pub. Date: Feb. 17, 2005

(65) Prior Publication Data

US 2008/0192232 A1  Aug. 14, 2008

(30) Foreign Application Priority Data

Aug. 8, 2003 (JP) ............................. 2003-290329

(51) Int. Cl.
*G01J 3/30* (2006.01)
*G01J 3/00* (2006.01)

(52) U.S. Cl. .................. 356/300; 356/51; 356/301; 356/309; 356/311; 356/315

(58) Field of Classification Search .................. 356/51, 356/301–303, 309, 311, 315, 317, 437, 438
See application file for complete search history.

(56) References Cited

U.S. PATENT DOCUMENTS 4,405,237 A * 9/1983 Manuccia et al. ........... 356/301
4,573,792 A    3/1986 Kajiyama et al.
7,385,681 B2 * 6/2008 Ninomiya et al. .......... 356/5.01
2002/0118352 A1 8/2002 Ohzu et al.

FOREIGN PATENT DOCUMENTS

| JP | 59-10835   |   | 1/1984  |
|----|------------|---|---------|
| JP | 6-288858   |   | 10/1994 |
| JP | 9-178566   |   | 7/1997  |
| JP | 10-153416  | * | 6/1998  |

OTHER PUBLICATIONS

W. A. de Groot; "The Use of Spontaneous Raman Scattering for Hydrogen Leak Detection" 30th AIAA/ASME/SAE/ASEE Joint Propulsion Conference, Jun. 27-29, 1994, pp. 1-11. Cited in the International Search Report.
International Search Report, dated Jul. 27, 2004 of PCT/JP2004/008038.

* cited by examiner

*Primary Examiner*—Layla G Lauchman
(74) *Attorney, Agent, or Firm*—Westerman, Hattori, Daniels & Adrian, LLP.

(57) ABSTRACT

A method for monitoring hydrogen gas and a hydrogen flame wherein an object light having a wavelength of about 309 nm and resulting from two or more laser beams, which have been irradiated to a space to be monitored, is collected and converted to an electronic image, and the electronic image is amplified and converted back to an optical image, thereby imaging a spatial intensity distribution of light at a specific wavelength. A device for monitoring hydrogen gas and a hydrogen flame, which comprises two or more laser beam sources, means for collecting an object light having a wavelength of about 309 nm and resulting from laser beams, which have been irradiated to a space to be monitored, image producing means for converting the object light to an electronic image, amplifying the electronic image, and converting back the amplified electronic image to an optical image, and means for imaging a spatial intensity distribution of light at a specific wavelength.

14 Claims, 4 Drawing Sheets

Emission spectrum of hydrogen flame (a) When laser beams of 355 nm and 416 nm were irradiated (b) When only laser beam of 355 nm was irradiated (c) When laser beam of 416 nm was irradiated

METHOD AND DEVICE FOR MONITORING HYDROGEN GAS AND HYDROGEN FLAME

TECHNICAL FIELD

The present invention relates to a technique for visualizing hydrogen gas and a hydrogen flame, which are not visible by the naked eye, in the form of visible images, thereby detecting a leakage of hydrogen gas and generation of a hydrogen flame from a far distance with safety and high accuracy. More particularly, the present invention relates to a method and a device for monitoring hydrogen gas and a hydrogen flame, which are suitably used with operations of hydrogen gas utilization facilities, such as hydrogen supply stations and fuel cells, which can perform continuous monitoring with less false detection.

BACKGROUND ART

Hitherto, a leakage of flammable gas has been detected by bringing sucked gas to direct contact with a sensor portion, and by measuring a gas concentration based on a change in value of electrical resistance, current, etc. However, the known gas detector is of the sensor type that a region capable of being monitored by one detector is narrow and a gas leakage cannot be detected unless the leaked gas reaches the detector. Accordingly, there has been a risk that, in spite of the event of a gas leakage, an alarm is not issued depending on the direction of wind and the position where the detector is installed. Another problem is that, in a gas refinery or the like, a very large number of gas detectors must be installed and a substantial cost is required (see Patent Reference 1).

On the other hand, to overcome the above-mentioned problem, there is proposed a gas visualizing device for monitoring the presence of a gas leakage from a far distance. The proposed gas visualizing device comprises a laser beam source for irradiating an infrared laser beam that contains an absorption wavelength of gas to be measured, and an image sensor for imaging absorption of the infrared ray reflected from the background by leaked gas so that the leaked gas is displayed in the form of a two-dimensional visible image.

However, such a known gas visualizing device requires a very large-sized and high-power laser beam source and therefore has a serious problem in point of cost. Another problem is that the displayed two-dimensional image is greatly affected by weather conditions and temperatures, and a difficulty arises in discriminating the occurrence of a gas leakage from shinning of sunlight. For those reasons, the known gas visualizing device has not been suitable for monitoring a gas leakage in practical fields (see Patent Reference 2).

Patent Document 1: Japanese Patent Laid-open No. 6-307967
Patent Document 2: Japanese Patent Laid-open No. 6-288858

DISCLOSURE OF THE INVENTION

Problems to be Solved by the Invention

Hydrogen gas is colorless, transparent and odorless. In environments utilizing and storing the hydrogen gas, it has been usual that a gas leakage is monitored by installing a stationary flammable-gas detector in a place where the gas tends to reside, while the leakage point is located by personnel carrying a portable gas detector and going round for inspection. Accordingly, there has been demanded a monitoring technique capable of detecting a gas leakage and locating the leakage point in a continuous manner.

Also, a device for detecting ultraviolet rays generated from flames and issuing an alarm has been put into practical use. In the case of a hydrogen flame that is invisible to the naked eye under sunlight in the daytime, however, it has been difficult to take an optimum action because of incapability in safely locating the ignition point even with such a device being operated. In addition, that device covers a wide range of wavelength of ultraviolet rays as a detection target and therefore may detect even an ultraviolet ray (e.g., sunlight reflected by a window glass) other than those generated from flames in some cases. This leads to a problem that the device is susceptible to malfunction and reliability is insufficient.

Further, when trying to monitor hydrogen gas and a hydrogen flame at the same time, the wavelength for monitoring the hydrogen gas often differs from the wavelength for monitoring the hydrogen flame. To be adapted for such a case, a mechanism for switching over the monitoring wavelength or detectors for measuring both the monitoring wavelengths are required, thus resulting in a problem that the device construction is complicated.

In addition, when trying to observe the Raman scattering light of hydrogen gas with irradiation of a laser beam, a problem arises in that the monitoring accuracy is reduced with noises generated by extraneous lights. There are three kinds of extraneous lights to be taken care of, i.e., (i) sunlight, (ii) reflected light, and (iii) fluorescence generated from wall materials, water, oil films, etc. which are present within the monitoring space. In particular, the fluorescence caused by the laser beam appears over a wide wavelength range on the side longer than the wavelength of the irradiated laser beam and impedes the detection of the hydrogen gas. However, a method for coping with such a problem from a fundamental point of view is not yet proposed.

In order to overcome the above-mentioned problems, an object of the present invention is to provide a method and a device for monitoring hydrogen gas and a hydrogen flame with high accuracy by visualizing the hydrogen gas and the hydrogen flame, which are not visible by the naked eye, in the form of visible images, and by incorporating features for eliminating extraneous lights.

Summary of the Invention

The present invention has been made with intent to meet a strong demand for overcoming the above-mentioned problems, and detects a leakage of hydrogen gas by utilizing a Raman scattering phenomenon that, when a laser beam is irradiated to a target, the wavelength of the laser beam is shifted by an amount corresponding to energy that is equivalent to the absorption energy of a target molecule, and by imaging a spatial intensity distribution of the Raman scattering light.

While the wavelength of the Raman scattering light generated from hydrogen gas can be changed by varying the wavelength of the irradiated laser beam, laser devices selectable in practical use are limited. In the present invention, therefore, the wavelength of a laser beam source is selected such that the wavelength for monitoring hydrogen gas is the same as the wavelength of an ultraviolet emission spectrum generated from a hydrogen flame.

Also, noises caused by extraneous lights are minimized as follows.

To reduce the influence of sunlight, a time gate used for picking up an image is set to be short. More specifically, the influence of sunlight of which intensity is weak in a short time can be minimized by observing only the Raman scattering light from hydrogen gas, which is generated in the pulse-like form for a short time upon irradiation of a laser beam having a short pulse width.

To reduce the influence of reflected light, the width of transmission wavelength of an optical band-pass filter is narrowed. In other words, only an ultraviolet ray emitted from hydrogen gas or a hydrogen flame can be detected by narrowing a wavelength range of the detectable ultraviolet ray.

To reduce the influence of fluorescence, a wavelength corresponding to the anti-Stokes Raman scattering wavelength is employed as the monitoring wavelength. More specifically, fluorescence always appears at a wavelength longer than that of the irradiated laser beam, the influence of fluorescence can be reduced by monitoring the anti-Stokes light having a shorter wavelength than the laser beam. However, the anti-Stokes light is very weak and is usually hard to measure. As a feature for overcoming such a problem, one laser beam and another laser beam having a wavelength matched with the Raman spectrum wavelength of hydrogen are mixed with each other to generate a stronger anti-Stokes Raman scattering light.

The present invention provides a method for monitoring hydrogen gas and a hydrogen flame, as set forth in (1)-(7) given below.

(1) A method for monitoring hydrogen gas and a hydrogen flame, wherein an object light having a wavelength of about 309 nm and resulting from two or more laser beams, which have been irradiated to a space to be monitored, is collected and converted to an electronic image, and the electronic image is amplified and converted back to an optical image, thereby imaging a spatial intensity distribution of light at a specific wavelength.

(2) In the method for monitoring hydrogen gas and a hydrogen flame set forth in above (1), the laser beams are emitted from a laser beam source with at least one wavelength of about 355 nm and a laser beam source with at least one wavelength of about 416 nm.

(3) In the method for monitoring hydrogen gas and a hydrogen flame set forth in above (1) or (2), the laser beams are each irradiated in the form of a pulse, and reception of the object light is turned on/off in sync with a laser beam irradiation pulse to collect the object light only in a time zone during which the object light is emitted.

(4) In the method for monitoring hydrogen gas and a hydrogen flame set forth in any one of above (1) to (3), a dye laser, a titanium sapphire laser, an optical parametric oscillation laser, or a hydrogen Raman cell is used as the laser beam source of about 416 nm.

(5) In the method for monitoring hydrogen gas and a hydrogen flame set forth in any one of above (1) to (4), a background image of the space to be monitored is picked up, and the background image is imposed on the image of the spatial intensity distribution of light at the specific wavelength.

(6) In the method for monitoring hydrogen gas and a hydrogen flame set forth in above (5), the background image is picked up with an imaging process insensitive to wavelengths of 309 nm, 355 nm and 416 nm.

(7) In the method for monitoring hydrogen gas and a hydrogen flame set forth in any one of above (1) to (6), the hydrogen gas is monitored when the laser beams are irradiated, and the hydrogen flame is monitored when the laser beams are not irradiated.

Also, the present invention provides a device for monitoring hydrogen gas and a hydrogen flame, as set forth in (8)-(14) given below.

(8) A device for monitoring hydrogen gas and a hydrogen flame, the device comprising two or more laser beam sources, means for collecting an object light having a wavelength of about 309 nm and resulting from laser beams irradiated to a space to be monitored, image producing means for converting the object light to an electronic image, amplifying the electronic image, and converting back the amplified electronic image to an optical image, and means for imaging a spatial intensity distribution of light at a specific wavelength.

(9) In the device for monitoring hydrogen gas and a hydrogen flame set forth in above (8), the two or more laser beam sources are a laser beam source with at least one wavelength of about 355 nm and a laser beam source with at least one wavelength of about 416 nm.

(10) In the device for monitoring hydrogen gas and a hydrogen flame set forth in above (8) or (9), each of the laser beam sources irradiates the laser beam in the form of a pulse, and reception of the object light is turned on/off by an image intensifier in sync with a laser beam irradiation pulse to collect the object light only in a time zone during which the object light is emitted.

(11) In the device for monitoring hydrogen gas and a hydrogen flame set forth in any one of above (8) to (10), a dye laser, a titanium sapphire laser, an optical parametric oscillation laser, or a hydrogen Raman cell is used as the laser beam source of about 416 nm.

(12) In the device for monitoring hydrogen gas and a hydrogen flame set forth in any one of above (8) to (11), the device further comprises means for picking up a background image, and means for superimposing the background image picked up by the image pickup means on the image of the spatial intensity distribution of light at the specific wavelength.

(13) In the device for monitoring hydrogen gas and a hydrogen flame set forth in above (12), the image pick-up means is insensitive to wavelengths of 309 nm, 355 nm and 416 nm.

(14) In the device for monitoring hydrogen gas and a hydrogen flame set forth in any one of above (8) to (13), the hydrogen gas is monitored when the laser beams are irradiated, and the hydrogen flame is monitored when the laser beams are not irradiated.

Advantages of the Invention

According to the present invention, since only ultraviolet images of the emission light of the hydrogen flame and the Raman scattering light from the hydrogen gas are selected and captured, it is possible to visually recognize the hydrogen flame and the hydrogen gas that are colorless and transparent.

According to the device of the present invention, because of no necessity of switching over the wavelength for observation, it is no longer required to prepare a plurality of light receiving units, and the device construction can be compacted correspondingly.

According to the present invention, influences of noises caused by extraneous lights, such as sunlight, reflected light, and fluorescence, can be minimized and highly accurate monitoring can be realized with less false detection.

Figure 1:
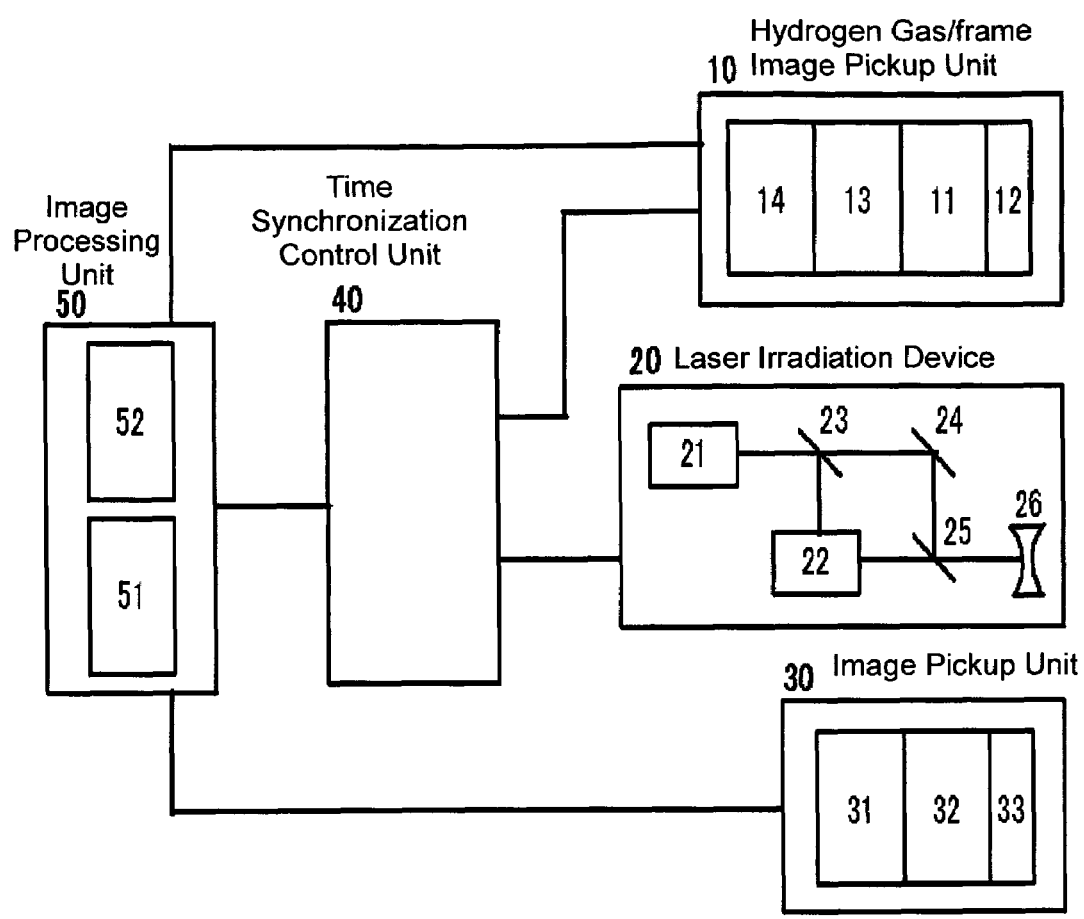
FIG. 1 is a block diagram showing the construction of a leakage gas imaging device 1 according to an embodiment of this application.

REFERENCE NUMERALS 10 hydrogen gas/flame image pickup unit
11 objective lens
12 optical band-pass filter (transmittable light selection means)
13 image intensifier (ultraviolet image capturing means)
14 electronic image pickup device
20 laser irradiation device
21 laser oscillator formed of Q-switch YAG laser emitting third harmonic (wavelength: 355 nm)
22 laser oscillator (wavelength: 416 nm) oscillated with optical pumping
23 laser beam distributor
24 mirror
25 mirror for overlapping laser beams
26 laser-beam expander lens
30 image pickup unit for picking up image of monitoring target region
31 electronic image pickup device
32 objective lens
33 shorter-wavelength cut optical filter
40 time synchronization control unit
50 image Processing unit
51 personal computer
52 display monitor

EMBODIMENTS

The present invention is based on the finding that when a laser beam of about 355 nm, which is given as a third harmonic of a generally used Q-switch YAG laser, and a laser beam of about 416 nm, which is obtained by causing optical pumping with a part of the 355-nm laser beam to produce oscillation at a wavelength corresponding to a Raman shift of hydrogen, are irradiated to hydrogen gas at the same time, the wavelength of a resulting Raman scattering light is exactly the same as 309 nm, i.e., the peak wavelength of an emission spectrum of an OH-group contained in a flame. A leakage of the hydrogen gas and generation of the hydrogen flame are detected by imaging a spatial intensity distribution of the light at 309 nm.

While one embodiment of the present invention is described below with reference to the drawings, the present invention is not limited to the following embodiment.

FIG. 1 shows the device construction according to the present invention. According to the embodiment of the present invention, reference numeral 10 in FIG. 1 denotes a first image pickup means, 20 denotes a laser irradiation device, 30 denotes a second image pickup means, 40 denotes a time synchronization control means, and 50 denotes an image processing means.

In the present invention, a visible image of a monitoring target region is picked up by the second image pickup means 30, an image of a hydrogen flame or hydrogen gas is picked up by the first image pickup means 10, and the image processing means 50 displays those two images in a superimposed relation. When hydrogen gas is monitored, the laser irradiation device 20 and the first image pickup means 10 are operated under control of the time synchronization control means 40 such that the image is picked up by the first image pickup means 10 in sync with laser irradiation.

A hydrogen gas leakage monitoring device includes an image pickup unit 10 as means for picking up respective images of gas and a flame. Reference numeral 11 in FIG. 1 denotes an objective lens as a collecting optical system, 12 denotes an optical band-pass filter serving as a transmittable light selection means, 13 denotes an image intensifier serving as an ultraviolet image capturing means, and 14 denotes an image pickup device. The objective lens 11 includes a lens and a barrel and is able to focus an image of an observation target on a photoelectric surface of the image intensifier 13.

More specifically, a photoelectric surface formed of a thin film and having an external photoelectric effect is disposed at an end of a housing of the image intensifier 13 on the side closer to the optical band-pass filter 12. An ultraviolet ray having passed through the optical band-pass filter 12 is converted to an electronic image by the photoelectric surface. The electronic image is converged by an electron lens and is subject to secondary electron multiplication by a microchannel plate. Then, the electronic image is converted back to an optical image by a fluorescent surface. As a result, the weak Raman scattering light induced from the hydrogen gas or the ultraviolet ray from the hydrogen flame is converted to a visible image. The visible image on the fluorescent surface of the image intensifier 13 can be electrically obtained as an image of the gas or the flame by using an eyepiece and an electronic image capturing device, so that the colorless and transparent gas and flame can be monitored.

The hydrogen gas leakage monitoring device includes a laser irradiation unit 20 for inducing the Raman scattering light from the hydrogen gas. Reference numeral 21 denotes a laser oscillator in the form of a Q-switch YAG laser emitting a third harmonic (wavelength: about 355 nm), and 22 denotes a laser oscillator (wavelength: about 416 nm) oscillated with optical pumping caused by the 355-nm laser beam. Reference numeral 23 denotes a laser beam distributor, 24 denotes a mirror, 25 denotes a mirror for overlapping the laser beams, and 26 denotes a laser-beam expander lens.

The laser beam of 355 nm emitted from the YAG laser oscillator 21 is distributed by the laser beam distributor 23, and a distributed part of the laser beam is irradiated to the optically pumped laser oscillator 22, whereby the laser oscillator 22 emits the laser beam of 416 nm. The laser beam having passed through the laser beam distributor 23 is reflected by the mirror 24 and then reflected again by the mirror 25 for superimposition of the two laser beams. As a result, the laser beams of 355 nm and 416 nm are irradiated to a space to be monitored through the laser-beam expander lens 26.

The optically pumped laser oscillator 22 can be constituted using a dye laser, a titanium sapphire laser, an optical parametric oscillator utilizing a nonlinear optical effect, or a hydrogen Raman cell.

With the construction described above, two units of light sources can be operated simultaneously for irradiation of two laser beams, while the device construction can be kept compact.

The wavelengths of the irradiated laser beams are 355 nm and 416 nm, and the wavelength for observation is 309 nm, i.e., shorter than those of the irradiated laser beams. Further, fluorescence induced by the irradiated laser beams always appears in a wavelength range longer than those of the irradiated laser beams. It is therefore possible to prevent the influence of ambient fluorescence in the observation of the hydrogen gas.

The hydrogen gas leakage monitoring device includes a second image pickup unit 30 for picking up the monitoring target region as a background image. Reference numeral 31 denotes an electronic image pickup device, 32 denotes an objective lens, and 33 denotes a shorter-wavelength cut optical filter. A wavelength range for image pickup is set to be not shorter than about 420 nm by the shorter-wavelength cut optical filter 33. Wavelength select conditions of the image pickup unit 30 are set to make it not transmittable for or insensitive to at least the light of 309 nm corresponding to the wavelength of emission from an OH-group contained in the flame and the Raman scattering light from the hydrogen gas, and the lights of 355 nm and 416 nm corresponding to the wavelengths of the irradiated laser beams.

If the fluorescence caused upon the laser irradiation is so strongly observed as to adversely affect the second image pickup unit 30 for picking up the monitoring target region as a background image, the background image may be picked up in sync with the laser irradiation signal in a time zone where the laser beams are not irradiated.

The hydrogen gas leakage monitoring device includes a time synchronization control unit 40 for establishing a time sync relation between the laser irradiation unit 20 for inducing the Raman scattering light from the hydrogen gas and the image pickup unit 10 as means for picking up the Raman scattering light from the hydrogen gas. The image pickup unit 10 provided with the image intensifier and adapted for the ultraviolet ray and the laser irradiation unit 20 are connected to the time sync control unit 40 via respective cables.

When the hydrogen gas is monitored, a voltage applied to the electron lens of the image intensifier 13 is controlled in sync with a laser beam irradiation pulse so as to turn on/off reach of electrons to the microchannel plate such that the microchannel plate multiplies electrons only in the time zone where the Raman scattering light induced from the hydrogen gas with the laser irradiation is observed. As a result of that on/off gate operation, the influences of extraneous lights, i.e., sunlight, illumination light, and/or the flame, can be held minimum.

The light emitted from the OH-group contained in the hydrogen gas is continuously generated, while the Raman scattering light from the hydrogen gas is generated only for the time during which the laser beams are irradiated. It is therefore possible to discriminately observe the emission from the flame by receiving the light of 309 nm with the image pickup device in the time zone where the laser beams are not irradiated or in the state where the laser irradiation is stopped, and the Raman scattering light from the hydrogen gas by receiving the light of 309 nm with the image pickup device in sync with the time at which the laser beams are irradiated.

The hydrogen gas leakage monitoring device includes an image processing unit 50. Reference numeral 51 denotes a personal computer containing an image processing program, and reference numeral 52 denotes a display monitor. The image pickup unit 10 provided with the image intensifier and adapted for the ultraviolet ray, the image pickup unit 30 as means for picking up the background image, and the time sync control unit 40 are connected to the personal computer 51 via respective cables.

The personal computer 51 contains a monitoring control program for executing monitoring control and an image processing program. It also includes an input means such as a keyboard or a mouse.

The monitoring control program has the function of issuing an alarm in characters and sounds when the hydrogen gas or flame is detected, or of informing the detection of the hydrogen gas or flame to a monitoring office, etc. Alternatively, the monitoring control program may be set so as to stop supply of the target gas or to perform a fire fighting operation.

The image processing program has the function of displaying the image picked up by the image pickup unit 10 provided with the image intensifier and adapted for the ultraviolet ray and the image picked up by the image pickup unit 30 as means for picking up the background image in one monitor screen 52 at the same time. Thus, the respective images of the hydrogen flame and the hydrogen gas can be displayed in the background image in a superimposed relation while those images are colored in easily recognizable colors.

Figure 2:
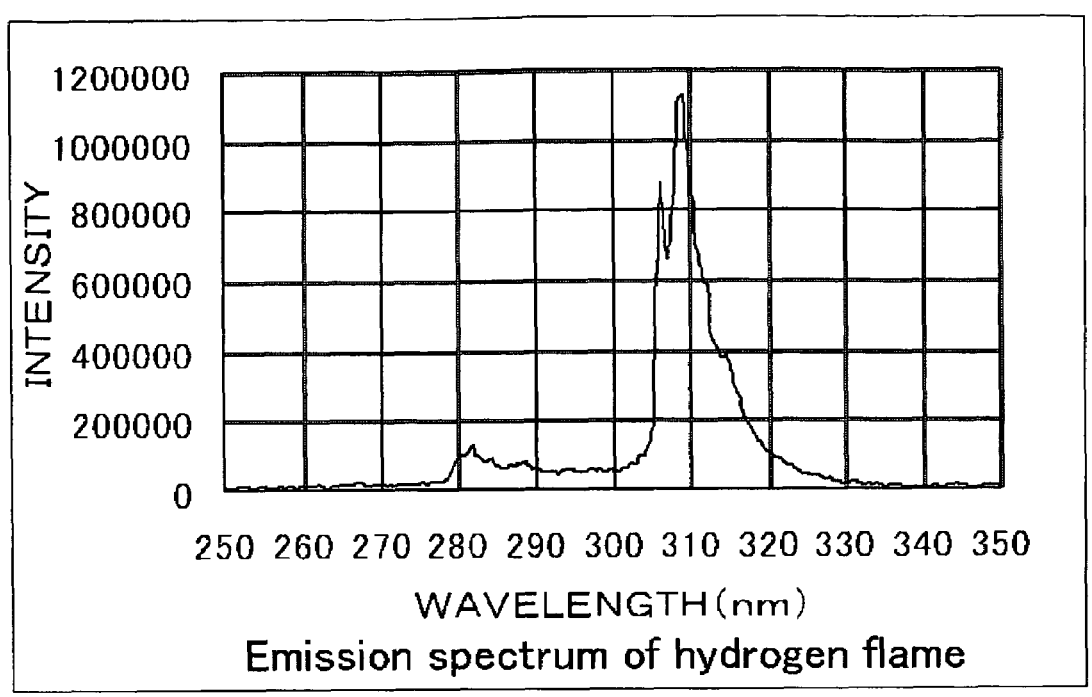
FIG. 2 is a graph showing an emission spectrum distribution of a hydrogen flame in an ultraviolet range.
Figure 3A:
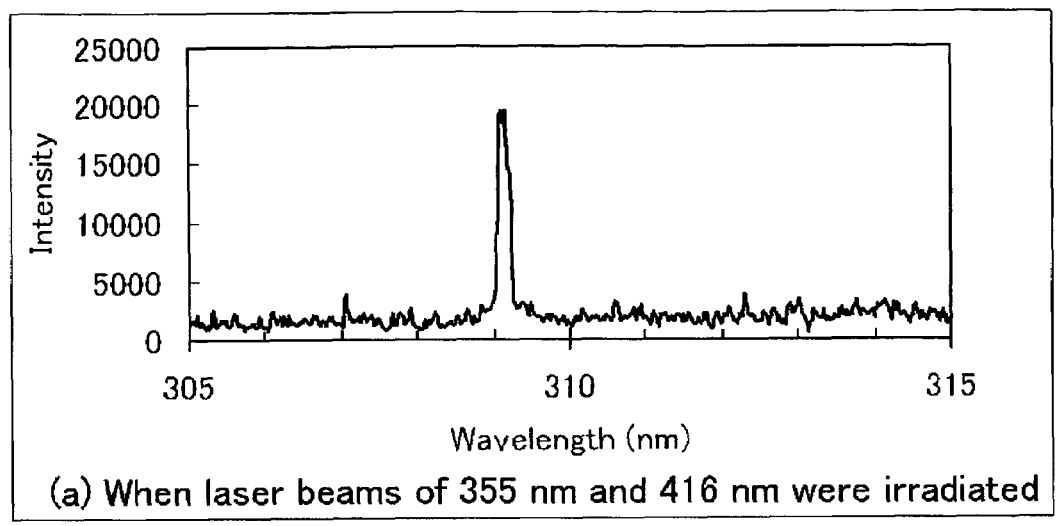
FIG. 3a is a graph showing a spectral distribution of the Raman scattering light emitted from hydrogen gas (when both laser beams of 355 nm and 416 nm were irradiated).
Figure 3B:
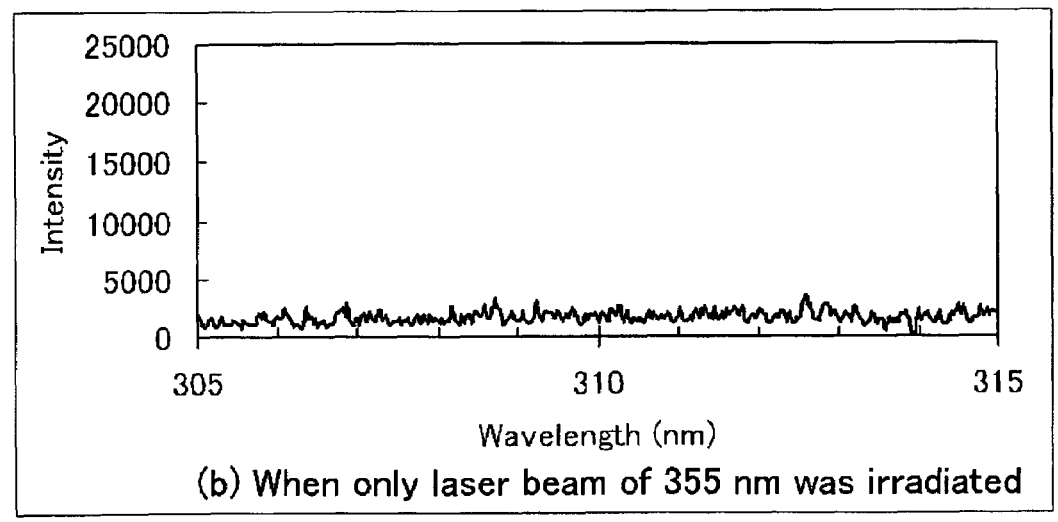
FIG. 3b is a graph showing a spectral distribution of the Raman scattering light emitted from hydrogen gas (when only the laser beam of 355 nm was irradiated).
Figure 3C:
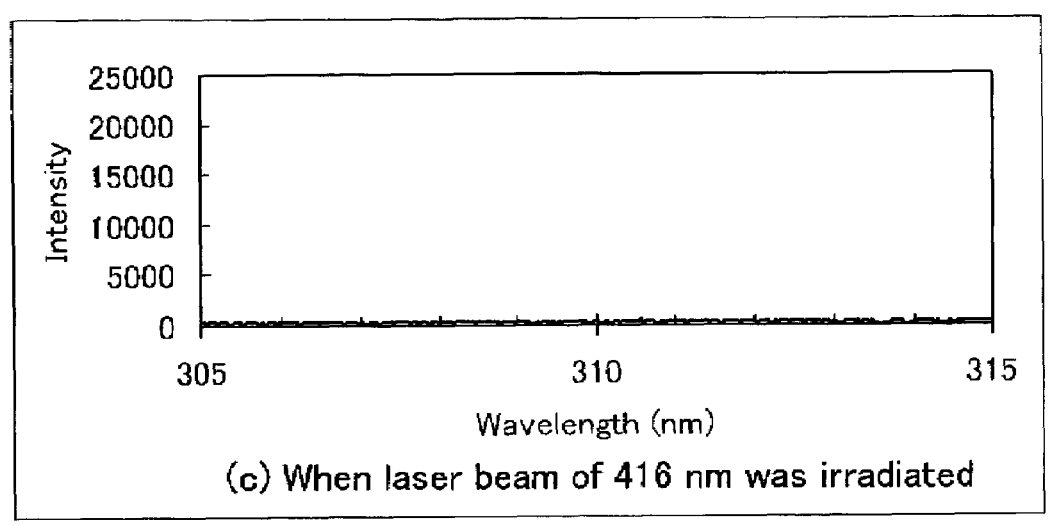
FIG. 3c is a graph showing a spectral distribution of the Raman scattering light emitted from hydrogen gas (when only the laser beam of 416 nm was irradiated).

FIGS. 2 and 3 show experimental data supporting the principle on which the present invention is based.

FIG. 2 shows an emission spectrum distribution in an ultraviolet range when hydrogen gas was burnt. In this experiment, the laser oscillation of the laser irradiation unit 20 was stopped. The emitted ultraviolet ray was received in a time zone of 1000 micro second.

The emission from the hydrogen flame was observed as having a peak at 309 nm and a spectrum width of ±5 nm. The intensity of a received signal was reduced as the time for observing the hydrogen flame (i.e., the light receiving time) was set to a shorter time. It was difficult to pick up an image of the hydrogen flame when the time zone for observation was set to 1 micro second or shorter.

FIG. 3 shows a spectral distribution when hydrogen gas was observed by irradiating the laser beam from the laser irradiation unit 20 to the hydrogen gas. In this experiment, a dye laser was used as the optically pumped laser oscillator 22, and the oscillation pulse width of each of the YAG laser and the dye laser was set to about 10 nano seconds. A dye was prepared by dissolving BIS-MSB (p-bis(o-methylstyryl)benzene) in dioxane at a concentration of 1 mmol. The light from the hydrogen gas was received in a time zone of 100 nano seconds after the laser irradiation. As seen from FIG. 3, the light of 309 nm was observed (FIG. 3(*a*)) when both the laser beams of 355 nm and 416 nm were irradiated at the same time. However, the light of 309 nm was not observed (FIGS. 3(*b*) and 3(*c*)) when one of the laser beams was cut.

Thus, by mixing the laser beams having different wavelengths, i.e., 355 nm and 416 nm, with each other, it is possible to monitor the hydrogen gas that cannot be observed in the case of irradiating one laser beam having either wavelength.

Further, since the peak wavelength of the Raman scattering light from the hydrogen gas and the peak wavelength of the ultraviolet emission from the hydrogen gas are exactly matched with each other, i.e., 309 nm, it is also possible to monitor the leakage of the hydrogen gas and the generation of the hydrogen flame by detecting the ultraviolet ray at the wavelength of 309 nm.

As described above, gas monitoring can be performed by operating the YAG laser 21 of the laser irradiation unit 20, and flame monitoring can be performed by stopping the YAG laser 21. Accordingly, the modes of monitoring the gas and the flame can be switched over just by selectively oscillating or stopping the YAG laser 21.

INDUSTRIAL APPLICABILITY

With the method and the device for monitoring hydrogen gas and a hydrogen flame according to the present invention, continuous monitoring can be realized in hydrogen gas utilization facilities, such as hydrogen supply stations and fuel cells, with less false detection.

The invention claimed is:

1. A method for monitoring hydrogen gas and a hydrogen flame, wherein an object light having a wavelength of about 309 nm and resulting from two or more laser beams, which have been irradiated to a space to be monitored, is collected and converted to an electronic image, and the electronic image is amplified and converted back to an optical image, thereby imaging a spatial intensity distribution of light at a specific wavelength.

2. The method for monitoring hydrogen gas and a hydrogen flame according to claim 1, wherein the laser beams are emitted from a laser beam source with at least one wavelength of about 355 nm and a laser beam source with at least one wavelength of about 416 nm.

3. The method for monitoring hydrogen gas and a hydrogen flame according to claim 1, wherein the laser beams are each irradiated in the form of a pulse, and reception of the object light is turned on/off in sync with a laser beam irradiation pulse to collect the object light only in a time zone during which the object light is emitted.

4. The method for monitoring hydrogen gas and a hydrogen flame according to claim 1, wherein a dye laser, a titanium sapphire laser, an optical parametric oscillation laser, or a hydrogen Raman cell is used as said laser beam source of about 416 nm.

5. The method for monitoring hydrogen gas and a hydrogen flame according claim 1, wherein a background image of the space to be monitored is picked up, and the background image is imposed on the image of the spatial intensity distribution of light at the specific wavelength.

6. The method for monitoring hydrogen gas and a hydrogen flame according to claim 5, wherein the background image is picked up with an imaging process insensitive to wavelengths of 309 nm, 355 nm and 416 nm.

7. The method for monitoring hydrogen gas and a hydrogen flame according to claim 1, wherein the hydrogen gas is monitored when the laser beams are irradiated, and the hydrogen flame is monitored when the laser beams are not irradiated.

8. A device for monitoring hydrogen gas and a hydrogen flame, the device comprising:
   two or more laser beam sources,
   means for collecting an object light having a wavelength of about 309 nm and resulting from laser beams irradiated to a space to be monitored,
   image producing means for converting the object light to an electronic image, amplifying the electronic image, and converting back the amplified electronic image to an optical image, and
   means for imaging a spatial intensity distribution of light at a specific wavelength.

9. The device for monitoring hydrogen gas and a hydrogen flame according to claim 8, wherein said two or more laser beam sources are a laser beam source with at least one wavelength of about 355 nm and a laser beam source with at least one wavelength of about 416 nm.

10. The device for monitoring hydrogen gas and a hydrogen flame according to claim 8, wherein each of said laser beam sources irradiates the laser beam in the form of a pulse, and
    reception of the object light is turned on/off by an image intensifier in sync with a laser beam irradiation pulse to collect the object light only in a time zone during which the object light is emitted.

11. The device for monitoring hydrogen gas and a hydrogen flame according to claim 8, wherein a dye laser, a titanium sapphire laser, an optical parametric oscillation laser, or a hydrogen Raman cell is used as said laser beam source of about 416 nm.

12. The device for monitoring hydrogen gas and a hydrogen flame according to claim 8, further comprising:
    means for picking up a background image, and
    means for superimposing the background image picked up by said image pickup means on the image of the spatial intensity distribution of light at the specific wavelength.

13. The device for monitoring hydrogen gas and a hydrogen flame according to claim 12, wherein said image pick-up means is insensitive to wavelengths of 309 nm, 355 nm and 416 nm.

14. The device for monitoring hydrogen gas and a hydrogen flame according to claim 8, wherein the hydrogen gas is monitored when the laser beams are irradiated, and the hydrogen flame is monitored when the laser beams are not irradiated.

* * * * *